(12) United States Patent
Nakajima

(10) Patent No.: US 9,307,956 B2
(45) Date of Patent: Apr. 12, 2016

(54) ULTRASONIC DIAGNOSTIC APPARATUS, IMAGE PROCESSING DEVICE, AND STAIN IMAGE GENERATING METHOD

(75) Inventor: Hideaki Nakajima, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 359 days.

(21) Appl. No.: 13/876,173

(22) PCT Filed: Sep. 21, 2011

(86) PCT No.: PCT/JP2011/071411
§ 371 (c)(1),
(2), (4) Date: Mar. 27, 2013

(87) PCT Pub. No.: WO2012/043312
PCT Pub. Date: Apr. 5, 2012

(65) Prior Publication Data
US 2013/0182120 A1    Jul. 18, 2013

(30) Foreign Application Priority Data

Sep. 28, 2010 (JP) ................................ 2010-217585

(51) Int. Cl.
*G01S 15/89* (2006.01)
*A61B 8/08* (2006.01)
*A61B 8/06* (2006.01)
(Continued)

(52) U.S. Cl.
CPC ... *A61B 8/52* (2013.01); *A61B 8/06* (2013.01); *A61B 8/481* (2013.01); *A61B 8/5215* (2013.01); *G01S 7/52071* (2013.01); *G01S 15/8979* (2013.01); *G06T 11/003* (2013.01)

(58) Field of Classification Search
CPC .............................. G01S 7/52041; A61B 8/06
USPC .......................................................... 348/163
See application file for complete search history.

(56) References Cited

U.S. PATENT DOCUMENTS 7,684,603 B2    3/2010  Hashimoto
8,861,812 B2   10/2014  Yoshikawa et al.
(Continued)

FOREIGN PATENT DOCUMENTS

CN    101170947 A    4/2008
CN    101332098 A   12/2008
(Continued)

OTHER PUBLICATIONS

International Search Report, International Application No. PCT/JP2011/071411, Filed Sep. 21, 2011, Mailed Oct. 18, 2011, ISA/Japanese Patent Office.
(Continued)

*Primary Examiner* — Jamie Atala
*Assistant Examiner* — Masum Billah
(74) *Attorney, Agent, or Firm* — Brundidge & Stanger, P.C.

(57) ABSTRACT

This ultrasonic diagnostic apparatus comprises: an operation unit with which a time division of a staining commencement time when a contrast agent enters is specified for each pixel of an ultrasonic image which is constructed chronologically with the ultrasonic diagnostic apparatus; and an image analyzing unit which determines a color assignment according to the time division of the staining commencement time, and applies a color to the pixel of the ultrasonic image with the determined color assignment, generating a contrast progress image.

11 Claims, 10 Drawing Sheets

(51) Int. Cl.
  *G01S 7/52*  (2006.01)
  *G06T 11/00*  (2006.01)

(56) References Cited

U.S. PATENT DOCUMENTS

| | | | |
|---|---|---|---|
| 2002/0103437 A1 | 8/2002 | Jibiki | |
| 2004/0215076 A1* | 10/2004 | Kamiyama | 600/443 |
| 2006/0067567 A1 | 3/2006 | Hashimoto | |
| 2008/0242988 A1 | 10/2008 | Yoshida et al. | |
| 2009/0299182 A1* | 12/2009 | Asafusa | 600/443 |
| 2010/0094133 A1* | 4/2010 | Yoshiara et al. | 600/453 |
| 2011/0075904 A1 | 3/2011 | Yoshikawa et al. | |
| 2011/0301465 A1* | 12/2011 | Waki | 600/445 |

FOREIGN PATENT DOCUMENTS

| | | |
|---|---|---|
| CN | 101416887 A | 4/2009 |
| CN | 101721226 A | 6/2010 |
| JP | 2714329 B2 | 2/1998 |
| JP | 2002-238901 | 8/2002 |
| JP | 2004-000739 | 1/2004 |
| JP | 2004304446 A | 10/2004 |
| JP | 2006122643 A | 5/2006 |
| JP | 2008264530 A | 11/2008 |
| JP | 2009-005755 | 1/2009 |
| JP | 2009-100971 | 5/2009 |
| JP | 2010-094220 | 4/2010 |
| WO | 2006-126684 | 11/2006 |
| WO | 2009110308 A | 9/2009 |
| WO | 2012-043312 | 5/2012 |

OTHER PUBLICATIONS

Japanese Office Action dated Oct. 6, 2015.

* cited by examiner

ULTRASONIC DIAGNOSTIC APPARATUS, IMAGE PROCESSING DEVICE, AND STAIN IMAGE GENERATING METHOD

FIELD OF THE INVENTION

The present invention relates to a technique for transmitting ultrasonic waves to the inside of a biological object and imaging the inside of the object using the received signals, particularly to a technique of imaging, from an image obtained using contrast medium, the inflow time range of the contrast medium.

DESCRIPTION OF RELATED ART

An ultrasonic diagnostic apparatus is one of the imaging apparatuses generally used in the medical field which include an MRI or CT apparatuses. The ultrasonic diagnostic apparatus is also smaller in size and is high in spatial resolution and time resolution compared to an MRI or CT.

In recent years, improvement of performance in medical diagnosis is expected, with the spread of ultrasonic contrast agent, due to the development of techniques in angiography and imaging of tumors using contrast agent. The ultrasonic contrast agent has the luminance value higher than the luminance value of the pixels in normal ultrasonic images which is differentiated from the pixels in normal ultrasonic images, which makes it easier for operators to observe the blood flow of an object into which contrast agent is injected.

Thus the staining process by ultrasonic contrast agent is considered effective for making diagnosis, as one of the indexes for evaluating the condition of target tissue. The difference in the staining process for each tissue indicates the hemodynamics of blood flow fluctuation such as a flow channel, flow volume or velocity of blood flow starting from a heart. For example, the hymodynamics in a staining process is different in accordance with the degree of proliferation or activity of a tumor, thus the properties of a tumor can be identified by closely observing the staining process.

In particular, the blood flow in the vicinity of or inside of a tumor shows not only the existence of a lesion but also the properties of the tissue, providing significant information for differential diagnosis.

A conventional technique is disclosed, for example in Patent Document 1. In Patent Document 1, image display is performed in the following procedure. First, plural frames of ultrasonic image data are acquired by scanning ultrasonic waves to an object into which contrast agent is injected. Next, inflow of contrast agent to each region is detected based on the signal intensity of the ultrasonic image data in the respective regions. Then the time point at which contrast agent enters in a region of interest set on an ultrasonic image is determined as a base time. On the basis of the base time, the relative times at which contrast agent enters the respective regions are obtained. Next, image data is generated in which the colors in the respective regions are presented by the hues corresponding to the relative times. Finally, an image showing the hues is displayed on a monitor.

In other words, different coloration display is to be performed for each time division to which an operator previously specifies blood vessel or tissue of different times at which contrast agent enters. In this manner, it is possible to visually identify to which time division a certain luminance in an ultimately displayed image belongs.

PRIOR ART DOCUMENTS

Patent Document

Patent Document 1: JP-A-2010-94220

SUMMARY OF INVENTION

Technical Problem

However, a problem still remains that while it is possible in Patent Document 1 to identify to which time division a certain luminance in an ultimately displayed image belongs, the progression of staining process using contrast agent still cannot be observed.

The objective of the present invention is to provide a technique capable of generating contrast progress images showing the progression state of the staining by contrast agent obtained from ultrasonic images.

BRIEF SUMMARY OF THE INVENTION

The present invention comprises an operation unit configured to specify a time division of a staining commencement time at which contrast agent enters for each pixel of ultrasonic images that are chronologically constructed by an ultrasonic diagnostic apparatus, and an image analyzing unit configured to determine a color assignment according to the time division of the staining commencement time and generate contrast progress images by applying colors to the pixels of the ultrasonic images with the determined color assignment.

Effect of the Invention

In accordance with the present invention, it is possible to generate contrast progress images showing the progress of a staining process using contrast agent obtained from ultrasonic images.

DETAILED DESCRIPTION OF THE INVENTION

Embodiment 1

Figure 1:
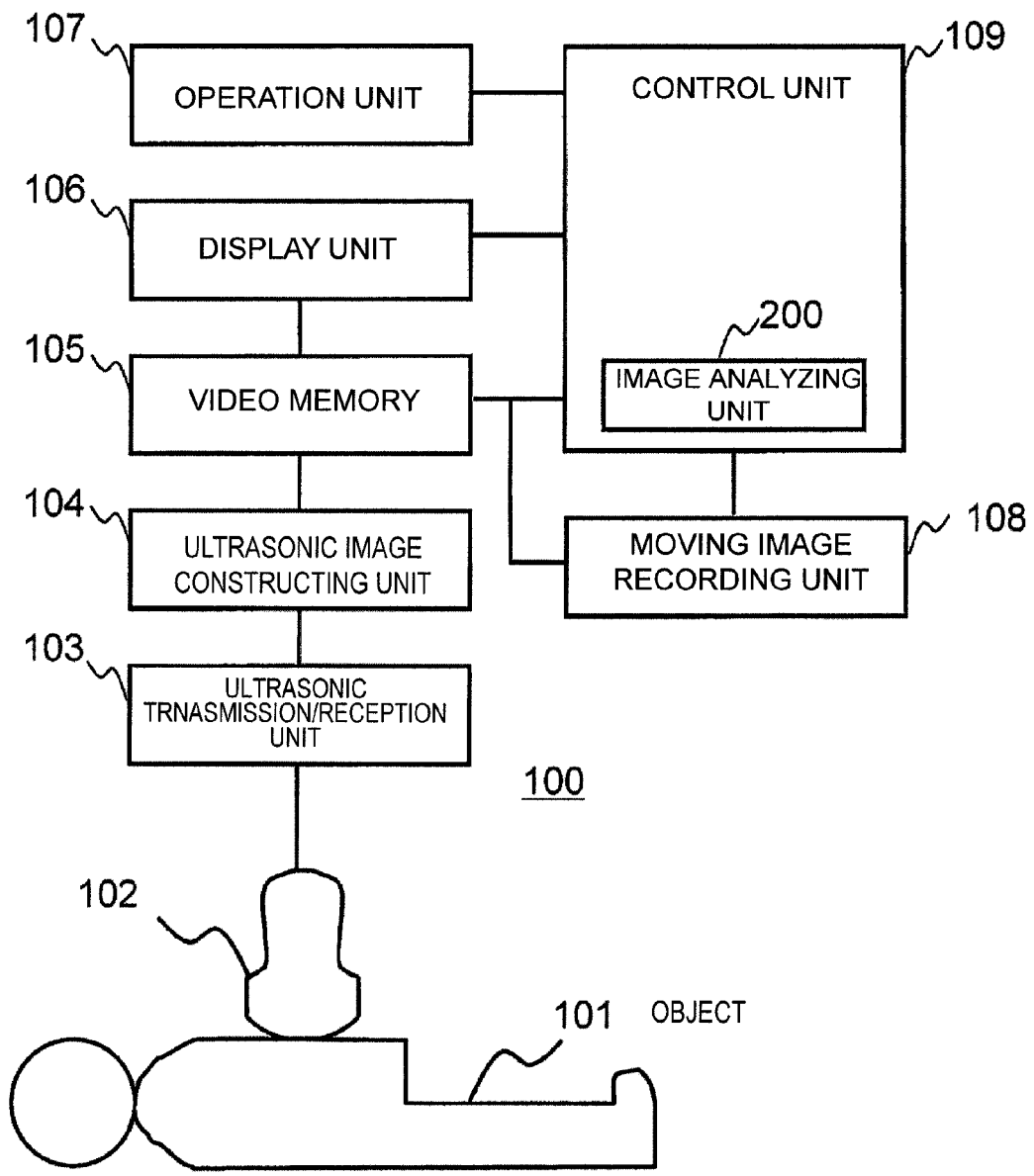
FIG. 1 is a block diagram of an ultrasonic diagnostic apparatus in Embodiment 1.

Embodiment 1 to which the present invention is applied will be described below. In the following description of all drawings for explaining the embodiments of the present invention, the same function parts are represented by the same reference numerals, and the duplicative description thereof is omitted.

FIG. 1 is a block diagram showing the configuration of an ultrasonic diagnostic apparatus 100 in Embodiment 1. The ultrasonic diagnostic apparatus 100 is for forming and displaying a 2-dimensional ultrasonic image or a 3-dimensional ultrasonic image of a diagnosis region using the reflected echo signal which is acquired by transmitting an ultrasonic wave to the inside of an object 101, comprising an ultrasonic probe 102 provided with transducer elements that irradiate and receive ultrasonic waves to and from the object 101, an ultrasonic transmission/reception unit 103 configured to transmit/receive ultrasonic signals, an ultrasonic image constructing unit 104 configured to construct a 2-dimensional ultrasonic image (B-mode image) or a 3-dimensional ultrasonic image on the basis of the reception signals, a video memory 105, a display unit 106, an operation unit 107, a moving image recording unit 108 and a control unit 109. Here, "moving images" indicate ultrasonic images that change with time obtained by an ultrasonic diagnostic apparatus, capable of obtaining ultrasonic images in almost real time and displaying the ultrasonic images as if they are moving images by transformation of the frames thereof.

The respective components of the apparatus will be described below in concrete terms. The ultrasonic probe 102 is provided with transducer elements arrayed by 1~m channels in the longitudinal direction of the ultrasonic probe 102. The ultrasonic probe 102 may also comprise transducer elements that are arrayed by 1~k channels in the minor-axis direction. In this case, focusing transmitting ultrasonic waves or receiving ultrasonic waves is performed also in the minor-axis direction by varying the delay times to be given to the respective transducer elements (1~k channels) in the minor-axis direction. Also, a transmission weight is applied by changing the amplitude of the ultrasonic transmission signal to be provided to the respective transducer elements in the minor-axis direction, as well as a reception weight is applied by changing the amplitude degree or attenuation degree of the ultrasonic reception signals from the respective transducer elements in the minor-axis direction. Further, aperture control can be carried out by turning on and off the respective transducer elements in the minor-axis direction.

To the ultrasonic probe 102, for example a CMUT (Capacitive Micromachined Ultrasonic Transducer: IEEE Trans. Ultrason. Ferroelect. Freq. Contr. Vol. 45 pp. 678-690 May 1998, etc.) can be applied, of which ultrasonic transmission/reception sensitivity, i.e. electromechanical coupling coefficient varies according to the magnitude of a bias voltage which is applied overlapping with a driving signal provided from the ultrasonic transmission/reception unit 103. A CMUT is a hyperfine volume type ultrasonic transducer manufactured by semiconductor microfabrication process (for example, LPCVD: Low Pressure Chemical Vapor Deposition).

The ultrasonic transmission/reception unit 103 supplies transmission signals and processes the received reflected echo signals to and from the ultrasonic probe 102, comprising a transmission circuit for controlling the ultrasonic probe 102 to output ultrasonic beams, a reception circuit for receiving the reflected echo signals of the output ultrasonic beams from the object 101 and collects the biological information, and a control circuit for controlling the previously-mentioned circuits.

The ultrasonic image constructing unit 104 converts the reflected echo signals processed in the ultrasonic transmission/reception unit 103 into an ultrasonic tomographic image, comprising a digital scan converter configured to form an ultrasonic image based on the sequentially input reflected echo signals, and a storage device formed by a magnetic disk that stores ultrasonic images, and a RAM. It processes the reflected echo signals received by the ultrasonic transmission/reception unit 103, converts the received signals into a 2-dimensional ultrasonic image, 3-dimensional ultrasonic image or various Doppler images, and outputs the constructed images.

The video memory 105 stores the ultrasonic images to be displayed on the display unit 106. The display unit 106 regenerates and displays the ultrasonic images stored in the video memory 105, and is formed by a device such as a CRT monitor or a liquid-crystal display monitor. If the display unit 106 has a display memory of its own (not shown in the drawing), 2-dimensional ultrasonic images, 3-dimensional ultrasonic images or various Doppler images output from the ultrasonic image constructing unit 104 can be displayed using the display memory without using the video memory 105.

The operation unit 107 is an input means that receives the commands from an operator or the setting and modification of parameters, and is formed by devices such as a keyboard or a touch panel. The parameters to be received by the operation unit are related to image quality or moving image recording.

The moving image recording unit 108 stores the ultrasonic images to be displayed on the display unit 106 via the video memory 105 as moving image data.

The control unit 109 controls the respective components of the ultrasonic diagnostic apparatus 100, and performs image analyzing process on the ultrasonic images stored in the moving image recording unit 108. The control unit 109 comprises a CPU, a memory and a storage unit, and performs controlling and image processing of the respective components by carrying out the programs stored in advance in the storage unit by loading them to the memory. The storage unit stores not only the programs but also various parameters set by the operator via the operation unit or data to be used by CPU for processing and data to be generated during the processing.

Figure 2:
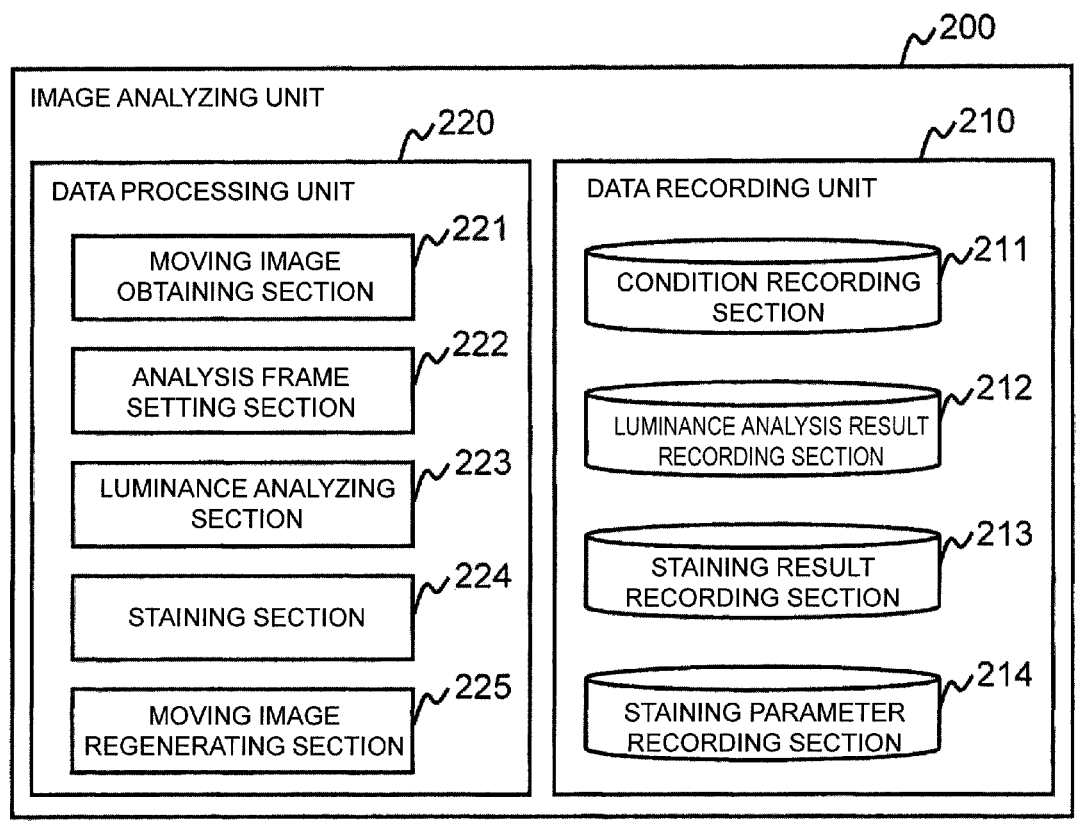
FIG. 2 is a functional block diagram of an image analyzing unit in Embodiment 1.

Next, the image analyzing process to be executed by the control unit 109 in Embodiment 1 will be described. In Embodiment 1, the control unit 109 comprises as shown in FIG. 1 an image analyzing unit 200 configured to analyze the ultrasonic images recorded as the moving image data in the moving image recording unit 108 and generates stained moving images. The operation unit 107 specifies a time division of a staining commencement time at which contrast agent enters for each pixel of the ultrasonic images (moving image data) that are chronologically constructed. The image analyzing unit 200 determines color assignments according to the specified time division of the staining commencement time, and generates contrast progress images by applying colors to the pixels on the ultrasonic images with the determined color assignments. In other words, by focusing on the variation of luminance in the respective pixels of moving image data, the moving image data is generated on which the staining is performed according to the time difference of entrance of contrast agent. In order to carry out this function, the image analyzing unit 200 in Embodiment 1 comprises a data recording unit 210 and a data processing unit 220 as shown in FIG. 2.

The data recording unit 210 comprises a condition recording section 211, a luminance analysis result recording section 212, a staining result recording unit 213 and a staining parameter recording unit 214.

The data processing unit 220 comprises a moving image obtaining section 221, an analysis frame setting section 222, a luminance analysis section 223, a staining section 224 and a moving image regenerating section 225.

The data to be recorded and the processing in the respective sections will be described below in detail.

The moving image obtaining section 221 obtains moving image data of an analysis target from the moving image recording section 108. When plural sets of moving image data are stored in the moving image recording section 108, the moving image obtaining section 221 obtains the moving image data specified by an operator. The operator specifies moving image data, for example, using the operation unit 107 via an analysis target moving image data setting region displayed on the display unit 106.

The analysis frame (range) setting section 222 receives the setting of the analysis range of the moving image data regarding the analysis target from the operator. The analysis range is the frame range in which the luminance analysis is to be performed by a luminance analyzing section 223 to be described later, and is to be specified by a starting frame and an ending frame. The received analysis range (a starting frame and an ending frame) is recorded in the condition recording section 211 in the data recording unit 210.

The analysis range is, for example from the timing (entrance commencement time) that contrast agent injected from a vein enters into a target region and the staining is started to the timing that the contrast agent is saturated. The operator inputs this analysis range using the operation unit 107 via, for example an analysis range specifying screen displayed on the display unit 106. Information such as a region for specifying the frame (analysis range specifying region) is displayed on the analysis range specifying screen along with the moving image data recorded in the moving image recording unit 108, and the operator specifies the analysis range while observing the moving images.

Figure 3:
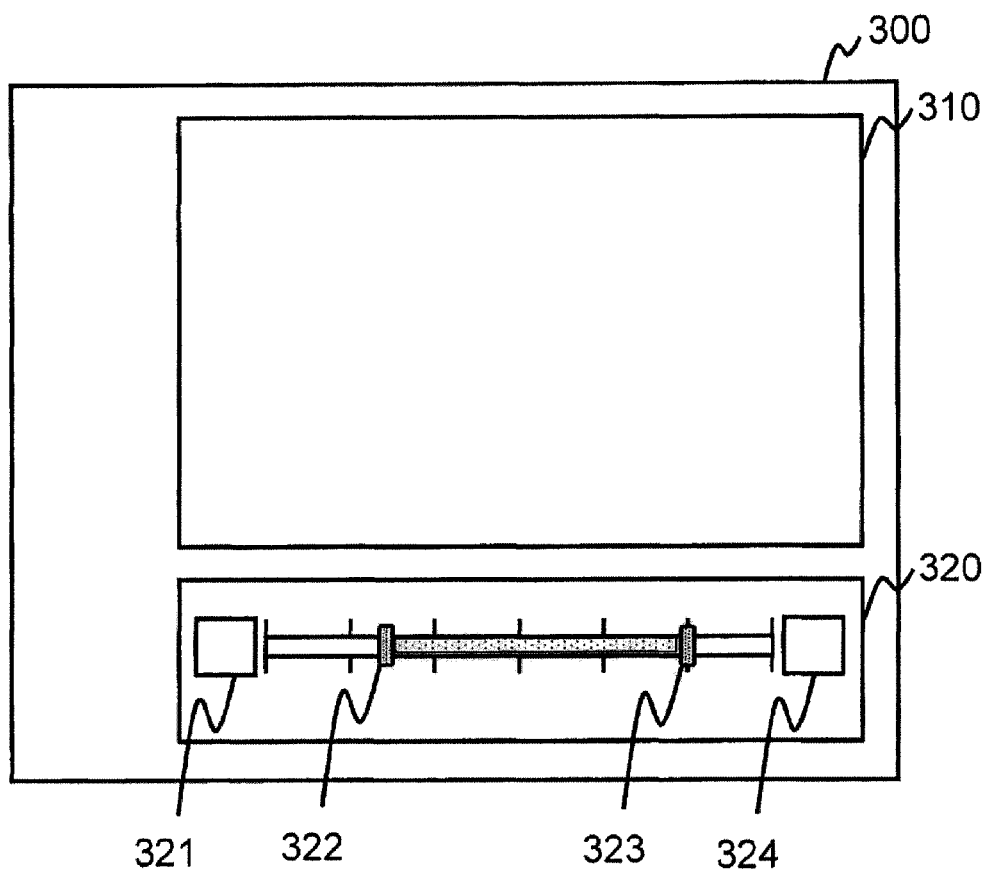
FIG. 3 is a view for explaining an analysis range specifying screen in Embodiment 1.

FIG. 3 shows an example of an analysis range specifying screen 300. As shown in the diagram, the analysis range specifying range 300 comprises a moving image data display region 310 and an analysis range specifying area 320. The moving image data which is the moving images recorded in the moving image recording unit 108 and is extracted by the operator as an analysis target is regenerated and displayed on the moving image data display area 310.

Also, the analysis range specifying area 320 receives the analysis range specified by the operator. Here, a case using a multi-slider is exemplified. The analysis range specifying area 320 comprises a starting frame slider 322 for setting a starting frame, an ending frame slider 323 for setting an ending frame, a starting frame display area 321 in which the frame number of a starting frame is to be displayed, and an ending frame display area 324 for displaying the frame number of an ending frame. The respective sliders and the frame numbers displayed on the respective display areas are synchronized, thus the frame numbers are changed along with the movement of the sliders. Also, by directly inputting the numeric values in the respective display areas, the positions of the sliders also change. A starting frame and an ending frame may be set by the sliders, or by directly inputting the frame numbers in the display areas.

The luminance analyzing section 223 performs a luminance analyzing process on the analysis range, in the moving image data obtained by the moving image obtaining section 221, set by the analysis frame setting section 222, and determines the staining commencement time of the respective pixels. The staining commencement time is the timing which enables identifying the time difference of the entrance of contrast agent, and is set in Embodiment 1 as time (threshold value luminance attainment time) $t\alpha$ at which the luminance of the contrast agent first reaches the previously determined luminance. Accordingly, the luminance analyzing section 223 in Embodiment 1 determines and outputs time (threshold value attainment time) $t\alpha$ which is spent from a starting frame to reach the previously defined luminance for each pixel.

Figure 4:
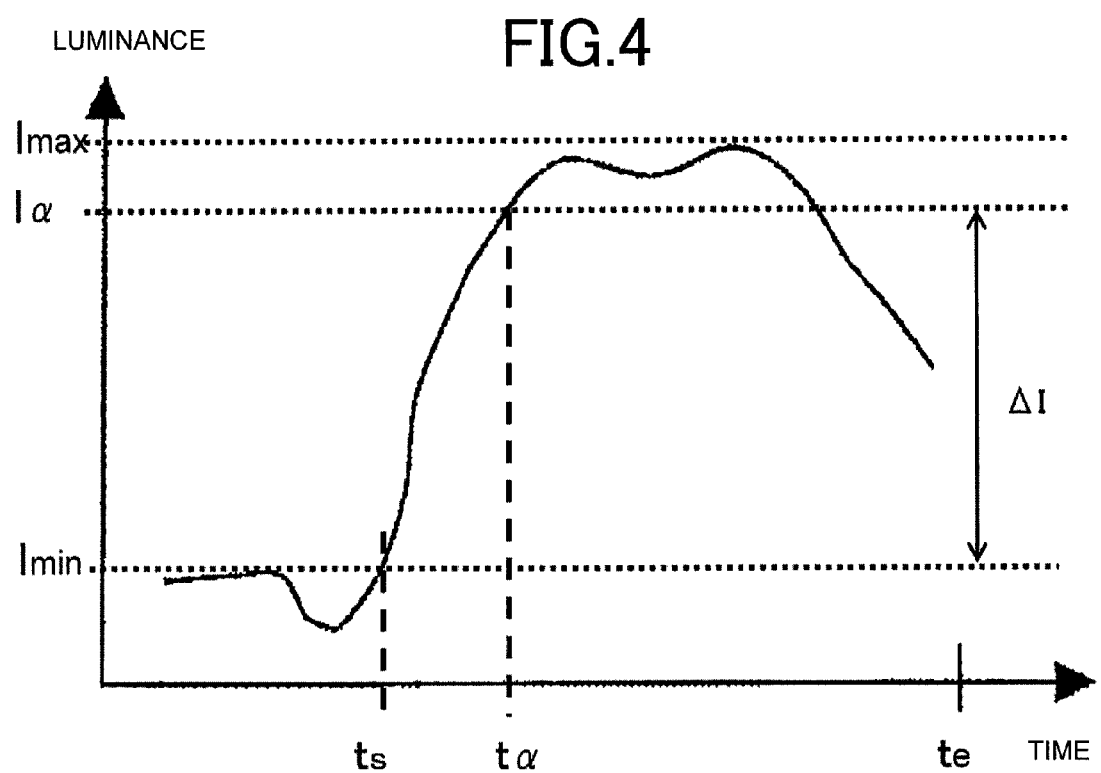
FIG. 4 is a view for explaining a method for determining a threshold luminance attainment time in Embodiment 1.

FIG. 4 is a view for explaining the means for determining threshold value luminance attainment time $t\alpha$ of specified pixels.

Here, the time at the starting frame of an analysis range is set as $\mu s$, and the time at the ending frame is set as te. As shown in the drawing, the luminance analyzing section 223 extracts maximum value Imax of the luminance in each pixel in the analysis range. Then value I$\alpha$ is obtained by multiplying the maximum value of the luminance by previously set threshold $\alpha$ (fixed value), and the time that the luminance reaches value I$\alpha$ is set as threshold value luminance attainment time $t\alpha$. For threshold value $\alpha$, for example 0.8 is used. The luminance analyzing section 223 records threshold luminance attainment time $t\alpha$ obtained in each pixel as the luminance analysis result in the luminance analysis result recording unit 212. At this time, not only threshold value luminance attainment time $t\alpha$ but also Imax and I$\alpha$ may also be recorded.

Figure 5:
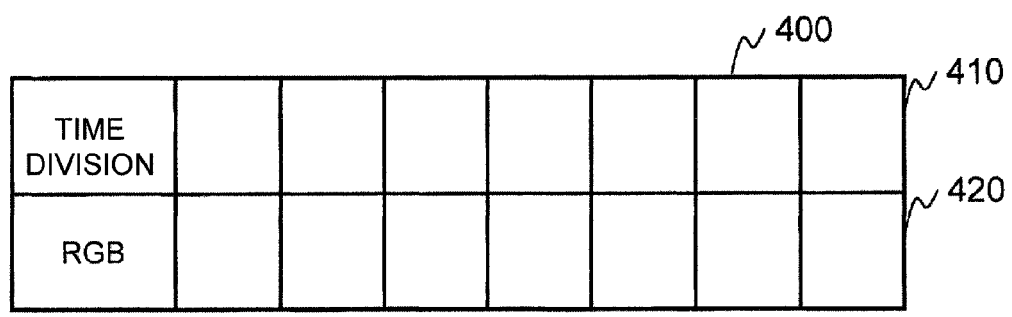
FIG. 5 is a view for explaining a color chart in Embodiment 1.

In the staining parameter recording unit 214, a color chart which stores a display color for each time range is recorded as a staining parameter. FIG. 5 shows an example of a color chart 400 to be stored. As shown in the drawing, time divisions 400 and colors 420 are stored in the color chart 400 while being related to each other. In time divisions 410 storage area, the time divisions for example, in which the elapsed time from the starting frame is divided into predetermined ranges are stored. In a color 420 storage area, the respective values are stored for specifying a display color in each time division.

The staining section 224 performs a staining process on the analysis range of the moving image data obtained by the moving image obtaining section 221 using the luminance analysis result of the luminance analyzing section 223. The staining process is the process for applying colors, with respect to each pixel, to the frames after the frame at which coloring (color assignment) is started (staining commencement frame). The staining commencement frame is the frame equivalent to luminance attainment time $t\alpha$, which is specified by luminance attainment time $t\alpha$ calculated by the luminance analyzing section 223 and the frame rate of the moving image data recorded in the moving image recording unit. Then the color assignment process is performed on the pixels in the frames after the staining commencement frame of the moving image data of an analysis target. For color assignment, display colors specified in colors 420 that are associated with the time divisions 410 equivalent to luminance attainment times $t\alpha$ and recorded in the color chart 400 are used. The processed moving image data is recorded in the staining result recording section 213 as contrast progress images (staining moving image data).

The moving image regenerating section 225, when receiving a command from an operator via the operation unit 107, regenerates the stained moving image data recorded in the staining result recording section 213 on the display unit 106.

Figure 6:
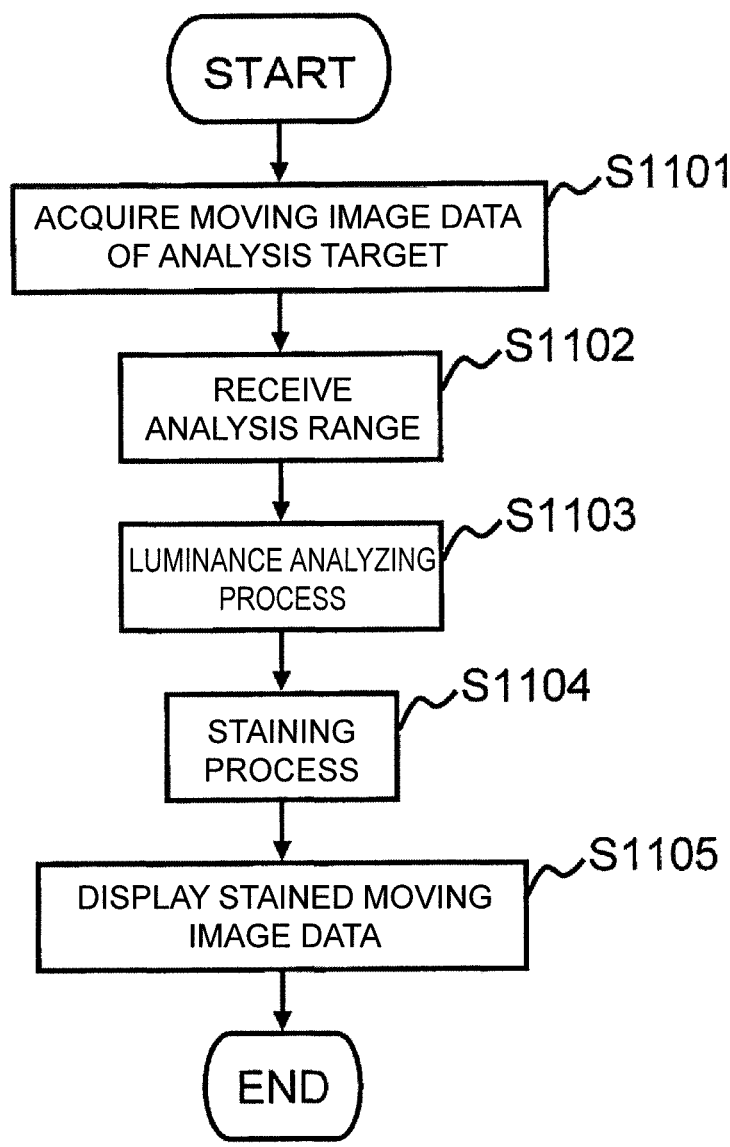
FIG. 6 is a flowchart of an image analyzing process in Embodiment 1.

Next, the flow of an image analyzing process in Embodiment 1 will be described, in which stained moving image data is generated by the image analyzing unit 200. FIG. 6 is a processing flow of the image analyzing process in Embodiment 1.

When a command to start an image analyzing process is received, the moving image obtaining section 221 obtains the moving image data of an analysis target from the moving image recording unit 108 (step S1011).

The analysis frame setting section 222 displays the moving image data obtained by the moving image obtaining section 221 on the display unit 106, and receives an analysis range (step S1102).

The luminance analyzing section 223 extracts the moving image in the analysis range from the moving image data to perform a luminance analyzing process (step S1103), and records the luminance analysis result in the luminance analysis result recording section 212.

Next, the staining section 224 performs the staining process using the luminance analysis result and the color chart 400 in the staining parameter recording section 214 (step S1104), and records the obtained contrast progress images (stained moving image data) in the staining result recording section 213.

The moving image regenerating section 225 waits for a command from the operator, and displays the contrast progress images (stained moving image data) on the display unit 106 (step S1105).

As described above, in accordance with Embodiment 1, by comprising the operation unit 107 configured to specify a time division of a staining commencement time at which contrast agent enters for each pixel of ultrasonic images that are chronologically constructed by an ultrasonic diagnostic apparatus and the image analyzing unit 200 configured to determine a color assignment according to the time division of the staining commencement time and generate contrast progress images by applying a color to the pixel in the ultrasonic images with the determined color assignment, it is possible to generate contrast progress images showing the progress of staining by contrast agent obtained from ultrasonic images.

In other words, with respect to the pixel of which the luminance value surpassed a predetermined value, the staining is performed after the surpassed time point with the display color in accordance with the surpassed timing. Therefore, it is possible to identify if the luminance value reached a predetermined value by whether or not the pixel is stained, as well as to obtain information on the elapsed time to reach the predetermined luminance value by a color (displayed color).

Also by obtaining such information for each pixel, the time change of the luminance associated with the inflow of contrast agent in an entire image can be presented to the operator.

Thus the state of luminance variation (staining progress) from the point at which contrast agent reached tissue can be objectively presented without any arbitrary operation or choice made by an operator.

In the staining section 224, luminance Imin of a starting frame may be extracted at the time of the staining process to calculate difference ΔI between Iα and Imin (see FIG. 4), so as to set the calculation result of a pixel of which Iα is smaller than Imin and a pixel which is smaller than noise value rmin that is previously defined by ΔI may be set as 0 instead of tα. The input of noise value rmin is received from the operator in advance via the operation unit 107, and set in the condition recording section 211. This process is carried out to eliminate the region where there is no perfusion of contrast agent from the color map. The parameters in the region where there is no perfusion of contrast agent cannot be calculated correctly and are often displayed as a noise on the stained moving image data. By carrying out the above-described process, visibility of the obtained stained moving image data can be improved.

Also, while threshold value luminance attainment time tα is specified using a threshold value in the above-described luminance analyzing process, the means does not have to be limited thereto. By analyzing the analysis range and defining in each pixel approximation TIC of a straight line in which a graph of luminance change is simplified by a given function, threshold value luminance attainment time Tα may be determined using the defined approximation. Also for reducing the load of the moving image recording unit 108, the information capable of specifying approximation TIC instead of moving image data may also be stored.

Also, the staining starting frame in Embodiment 1 is to be equivalent to threshold value luminance attainment time tα, the frame does not have to be limited thereto. For example, the frame may also be equivalent to a time such as an inflow starting time, equilibrium luminance attainment time, or disappearance starting time. These times may be set to be calculated using the above-mentioned approximation TIC. Also, a threshold luminance attainment time, inflow starting time, equilibrium luminance attainment time, disappearance starting time, etc. may be stored in the data recording unit 210 in advance as parameters for specifying a staining commencement time, so that the operator can select one before starting the analyzing process.

Also, the image analyzing unit 200 in Embodiment 1 may also comprise a TIC calculating section configured to calculate TIC for a region of interest (ROI) which is set by an operator in advance. In this case, the calculated TIC may be displayed on the display unit 106 along with the stained moving image data.

Also, the image analyzing unit may be configured capable of selecting stained moving image data or TIC from moving image data to be recorded in the moving image recording unit. For example, it may be configured capable of automatically identifying the necessity for generating TIC, for example by setting to calculate TIC when an ROI is set for generating TIC.

Also, by performing an image analyzing process by Embodiment 1 in prior to the generation of TIC to receive an ROI for generating TIC on the stained moving image data to be displayed on the display unit 106. In this manner, an ROI can be set with higher accuracy, since the ROI can be set on the moving image data with higher visibility and objectivity.

Further, only the final frame of the stained moving image data in Embodiment 1 may be displayed as a still image. By displaying the final frame, the difference of entrance times of contrast agent can be confirmed at one glance.

Also, the time division 410 in the color chart 400 is not limited to the time range as described above. For example, numbers to specify the time divisions 410 may also be stored. In this case, the staining section 224 evenly allots the respective divisions 410 in the analysis range set by the analysis frame setting section 222.

Also, the format of the color chart 400 is not limited to one type. Plural types of color charts may be provided to be selected by an operator. Also, the colors 420 to be corresponded to the respective time divisions 410 may be configured such that an operator can create colors of his/her choice. The number of time divisions 410 may also be set as variable. By increasing the number of time divisions, detailed observation can be carried out.

Embodiment 2

Next, Embodiment 2 to which the present invention is applied will be described. While the analysis range is set by an operator in Embodiment 1, the analysis range is automatically set in Embodiment 2 by the image analyzing unit. Embodiment 2 will be described below focusing on the configuration different from Embodiment 1.

The ultrasonic diagnostic apparatus 100 in Embodiment 2 has basically the same configuration as that of Embodiment 1.

In this regard, however, a data processing unit 200a of the image analyzing unit 200 in Embodiment 2 comprises an analysis frame determining section 226 in place of the analysis frame setting section 222.

Figure 7:
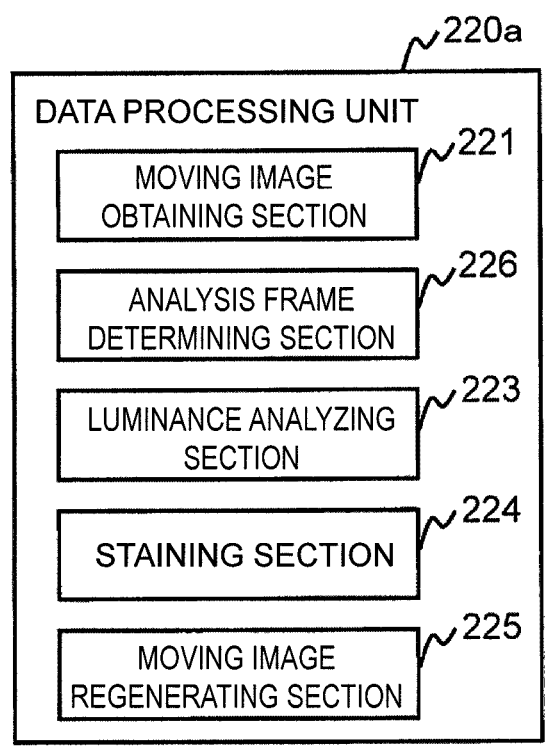
FIG. 7 is a functional block diagram of a data processing unit in Embodiment 2.

FIG. 7 is a functional block diagram of the data processing unit 220a in Embodiment 2.

The analysis frame determining section 226 in Embodiment 2 performs the analysis range determining process to determine the frame range (analysis range) to be analyzed by the luminance analyzing section 223 from the moving image data recorded in the moving image recording unit 108. As described above, the analysis range is from an inflow starting time to a disappearance time, and the analysis frame determining section 226 determines and outputs a starting frame and an ending frame equivalent to the respective times.

In Embodiment 2, for example, the flash time in the header information provided to moving images is set as an inflow starting time. In other words, the frame corresponding to this inflow starting time is set as a starting frame. The flash time is the time at which an ultrasonic wave that breaks down contrast agent is generated.

Also by calculating the sum of the signal intensities (luminance) in all pixels for each frame, the frame in which the difference of the sums compared to the adjacent frame is a predetermined value or more may be set as a starting frame.

Also, when the condition that the difference of the sum of the signal intensities from that in the adjacent frame is within a predetermined range for longer than predetermined time T, the frame which is immediately after predetermined time T is set as an ending frame.

The determined result is recorded in a range recording section in the storage unit 210 as an analysis range.

The rest of the configuration of the image analyzing unit 200 in Embodiment 2 is the same as in Embodiment 1.

Figure 8:
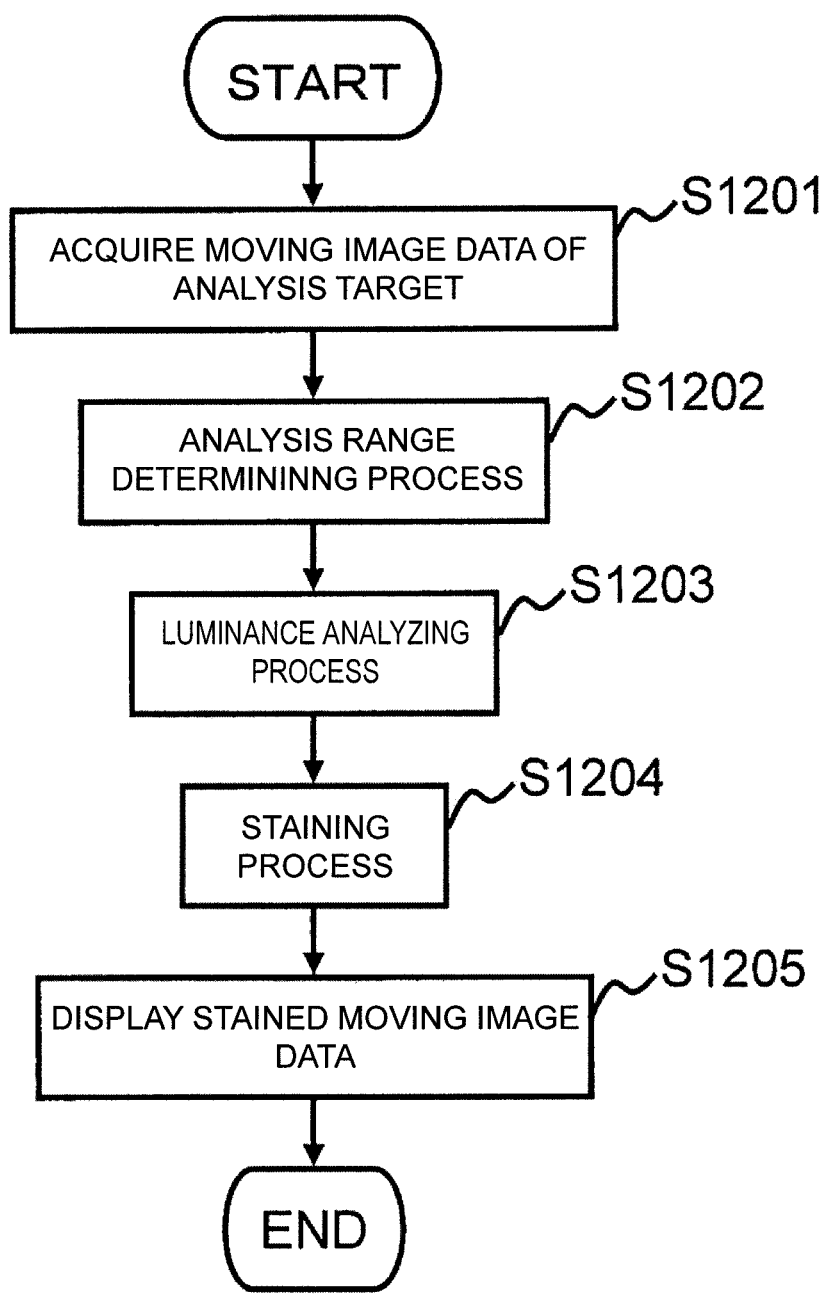
FIG. 8 is a flowchart of an image analyzing process in Embodiment 2.

Next, the flow of the image analyzing process by the image analyzing unit 200 in Embodiment 2 will be described. FIG. 8 is a processing flow of the image analyzing process by the image analyzing unit 200 in Embodiment 2.

When a command to start an image analyzing process is received, the analysis frame determining section 226 obtains the moving image data from the moving image recording section (step S1201). Then an analysis range determining process for determining the analysis range is executed (step S1202).

The luminance analyzing section 223 extracts the moving images in the analysis range from the moving image data to perform the luminance analyzing process (step S1203), and records the luminance analysis result in the luminance analysis result recording section 212.

Next, the staining section 224 performs the staining process using the luminance analysis result and the color chart 400 in the staining parameter recording section 214 (step S1204), and records the obtained stained moving image data in the staining result recording section 213.

The moving image regenerating section 225 waits for a command from an operator, regenerates the stained moving image data and displays the data on the display unit 106 (step S1205).

As described above, in accordance with Embodiment 2, the following particular effect can be achieved in addition to the advantage which can be attained by previously described Embodiment 1.

That is, the range which satisfies previously defined conditions is automatically determined as an analysis range for analyzing the luminance. Thus the analysis range which satisfies previously defined conditions can be determined accurately and swiftly compared to a case of determining the analysis range manually by an operator.

Also, in accordance with Embodiment 2, since an analysis range can be determined with high accuracy prior to the analyzing process, the accuracy of the analysis result can also be improved, in addition to the advantage in Embodiment 1.

Embodiment 2 can also be configured capable of generating approximation TIC using a previously specified region or the sum of the pixel values in all pixels and determining an analysis frame (a starting frame and an ending frame) using the generated TIC. In this case, the analysis frame determining section 226 generates approximation TIC.

Embodiment 3

Next, Embodiment 3 to which the present invention is applied will be described. In Embodiment 3, generated luminance analysis result and stained moving image data are stored being associated with the original moving image data. Then in a case that image analysis is commanded with respect to already processed moving image data, the processed data is extracted from the data recording unit instead of reprocessing the data.

At the time that moving image data is recorded in the moving image recording unit, a unique identification number (ID number) is given to each set of moving image data. In Embodiment 3, luminance analysis data and stained moving image data generated in the above-mentioned image analyzing unit 200 are managed by providing an ID number of the original moving image data. Therefore, the moving image obtaining section 221, at the time of obtaining the moving image data of an analysis target, obtains the ID number as well.

Figure 9:
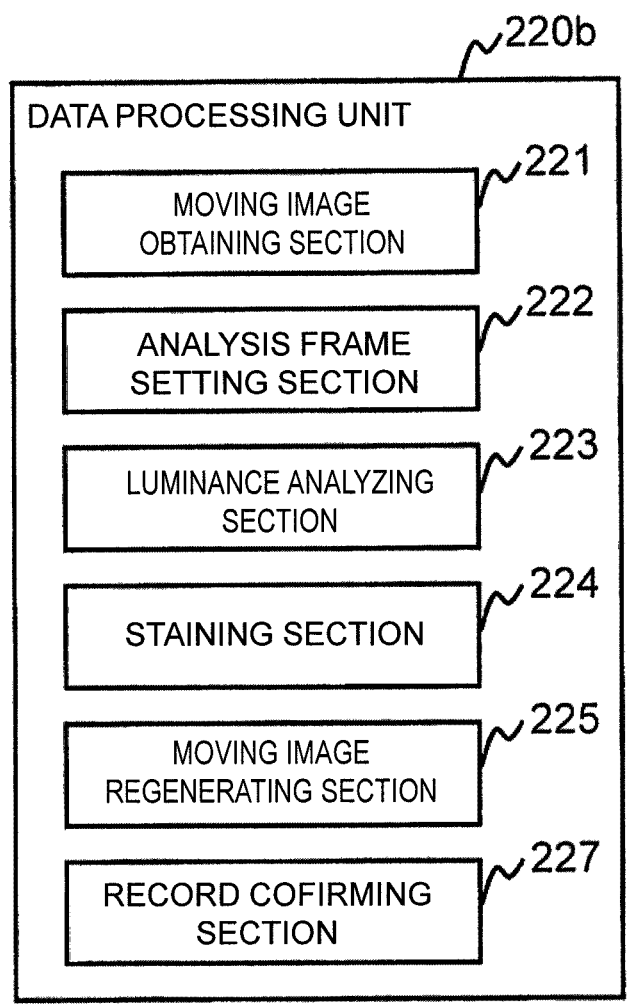
FIG. 9 is a functional block diagram of a data processing unit in Embodiment 3.

The ultrasonic diagnostic apparatus 100 in Embodiment 3 has basically the same configuration as in Embodiment 1 or Embodiment 2. In this regard, however, a data processing unit 200b of the image analyzing unit 200 in Embodiment 3 further comprises a record confirming section 227 as shown in FIG. 9. The record confirming section 227 confirms whether the stained moving image data generated from the moving image data of an analysis target is stored in the data recording unit 210, and issues commands to the respective components in accordance with the stored condition.

Figure 10:
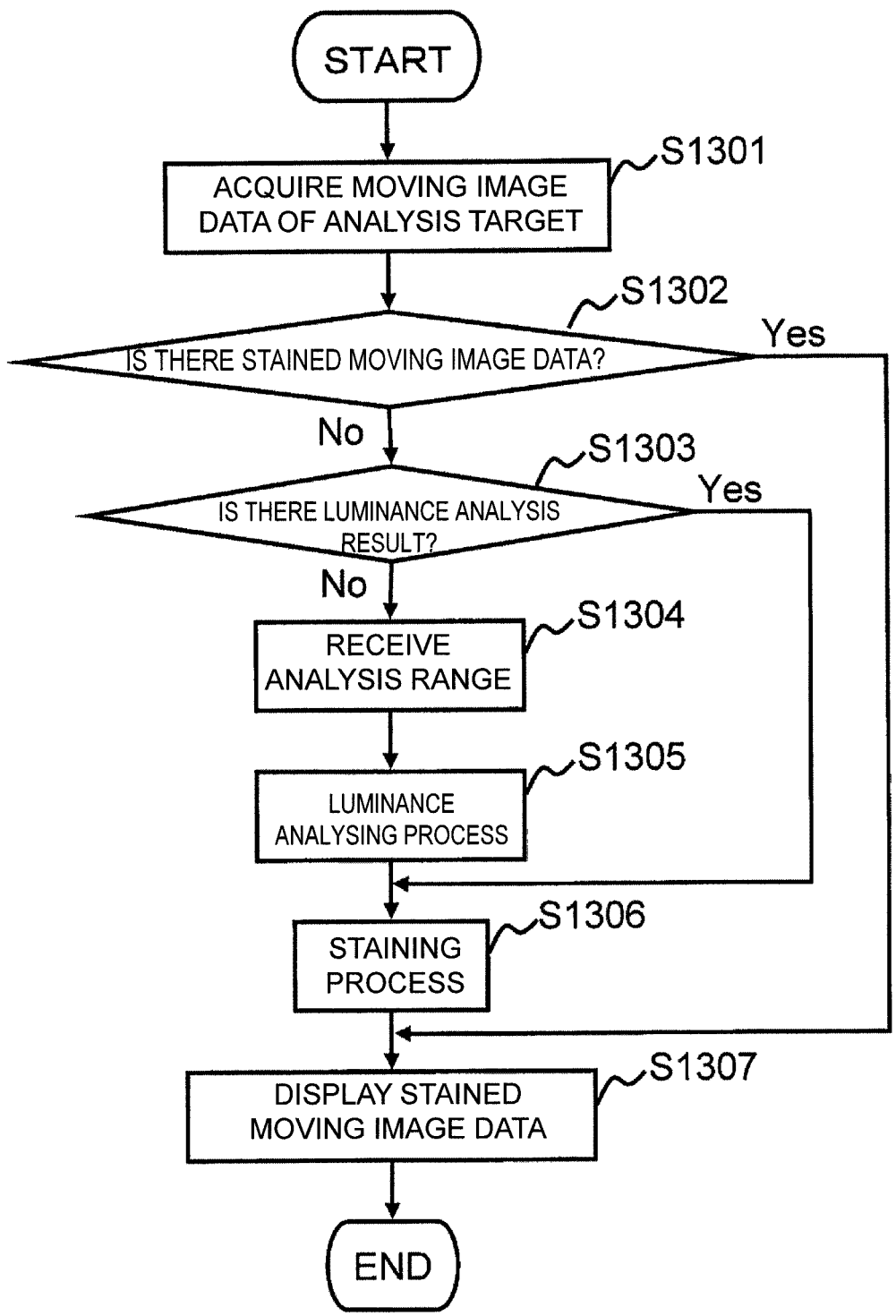
FIG. 10 is a flowchart of an image analyzing process in Embodiment 3.

On the basis of the configuration in Embodiment 1, the configuration of the respective components in Embodiment 3 will be described below in detail, focusing on the difference from Embodiment 1. The explanation will be provided along with the flow of the image analyzing process by the image analyzing unit 200 in Embodiment 3. FIG. 10 is a processing flow of the image analyzing process in Embodiment 3.

When a command to start an image analyzing process is received and the moving image obtaining section 221 obtains the moving image data of an analysis target with its ID number (step S1301), the record confirming section 227 extracts the ID number and detects the existence of the data corresponding to the extracted ID number referring to the staining result recording section 213 (step S1302).

When the stained data corresponding to the ID number is not stored, the record confirming section 227 refers to the luminance analysis result recording section 212 and detects the existence of the data corresponding to the ID number (step S1303). When the luminance analysis result corresponding to the ID number is not stored, the record confirming section 227 notifies the ID number to the analysis frame setting section 222. The analysis frame setting section 222, when receiving the notification, receives the analysis range (step S1304), and notifies the range and the ID number to the luminance analyzing section 223.

When the notification is received, the luminance analyzing section 223 performs the luminance analyzing process on the analysis range of the moving image data of the analysis target (step S1305), and records the luminance analysis result in the luminance analysis result with the corresponding ID number in the luminance analysis result recording section 212. Also, the luminance analyzing section 223 notifies the completion of the luminance analyzing process and the ID number to the staining section 224.

When the notification is received, the staining section 224 performs the staining process on the moving images obtained by the moving image obtaining section 221 using the luminance analysis result recorded in the luminance analysis recording section with the corresponding ID number (step S1306), and records the stained moving image data with the corresponding ID number in the staining result recording section 213.

Also, the staining section 224 notifies the completion of the staining process with the ID number to the moving image regenerating section 225. When the notification is received, the moving image regenerating section 225 extracts the stained moving image data corresponding to the ID number from the staining result recording section 213 to regenerate and display the data on the display unit 106 (step S1307).

On the other hand, when the luminance analysis result is stored with the ID number in step S1303, the record confirming section 227 notifies the staining section 224 the completion of the luminance analyzing process with the ID number. When the notification is received, the staining section 224 proceeds step S1306 to perform the staining process.

Also, when the stained moving image data is stored with the corresponding ID number in step S1302, the record confirming section 227 notifies the ID number and the command for regeneration of data to the moving image regenerating section 225. When the notification is received, the moving image regenerating section 225 proceeds step 1307 of obtaining the stained moving image data stored with the notified corresponding ID number from the staining result recording section 213 and displaying the regenerated data on the display unit 106.

As described above, in accordance with Embodiment 3, the following particular effect can be achieved in addition to the advantage attained by Embodiment 1 and Embodiment 2.

That is, the data once analyzed is stored in the data recording unit 210, and when a command for analyzing the same moving image data is received, the data is extracted from the data recording unit 210 to be displayed. Thus the repetition of performing the image analyzing process of Embodiment 3 on the same moving image data can be eliminated, whereby reducing the entire processing time.

Embodiment 3 is especially effective in cases such as a follow-up observation of a tumor which requires the above-described analysis on previously-obtained moving images.

In the above-described embodiment, when the luminance analysis result or stained moving image data generated from the processing target moving image data are found in the data recording unit 210, the respective processing is not to be carried out. The present embodiment is not limited to this, and it may also be configured, when the target imaging data is found in the data recording unit 210, to ask an operator whether or not to proceed the processing again.

Also, when the stained moving image data is found, an alternative such as to perform a staining process using another staining parameter may be provided, in addition to offering a choice of performing or not performing a re-staining process. By such configuration, stained moving image data can be obtained using different staining parameters, without performing luminance analysis.

The display 106 may be configured as capable of displaying plural sets of stained moving data at the same time. In this manner, plural regions can be observed at the same time, whereby saving the workload of an operator.

Also, plural areas may be provided for displaying plural sets of moving image data, by juxtaposing the respective sets of stained moving image data, or plural sets of stained moving image data may be synthesized to be displayed as one set of moving image data. The synthesis of data can be performed using a method such as calculating the difference of the pixel values in the respective pixels of each frame and applying display colors according to the differences.

For example, the synthesis method is effective in a case such as displaying stained moving images of before and after the RFA (radiofrequency ablation) treatment at the same time. In this case, different color charts 400 are used for the stained moving image data generated from the moving image data obtained before the treatment and the stained moving image data obtained after the treatment. For example, a staining pattern in shades of blue is used for the moving image data before the treatment, and a staining pattern in shades of red is used for the moving image data after the treatment. In this manner, the blood vessel into which contrast agent entered only before the treatment is displayed in blue, the blood vessel into which contrast agent is entered only after the treatment is displayed in red, and the blood vessel into which contrast agent is entered before and after the treatment is displayed in purple that is the blend of blue and red, which makes it easier to make comparison and possible to visualize the effect of the treatment at one glance.

Also, stained moving image data to be displayed on the display unit 106 may also be set as directly selectable from the staining result recording section 213. In this case, the display unit may be configured so that an operator can directly select ID numbers, or a table in which the data to be specified by the operator such as patient's names or imaging dates associated with the ID of the moving image data are stored can be provided so that the operator can specify the information such as the patient's name or the imaging date.

Embodiment 3 manages luminance analysis results and stained moving image data using ID numbers based on the original moving image data by which the previously mentioned data are generated, but data management means is not limited thereto. For example, management numbers which are separate from the ID numbers of moving image data and independent in the image analyzing unit 200 may also be used. In this case, a table for corresponding ID numbers of moving image data to the management numbers is further comprised, and the record confirming section 227 executes processing referring to the table.

The ultrasonic diagnostic apparatus in the above-described respective embodiments may also comprise a transmission/reception interface for transmitting/receiving data to/from an external device and a function to transmit/receive generated luminance analysis results and stained moving image data to/from an external device via the transmission/reception interface. Also, in a case that luminance analysis results and stained moving image data are stored being associated with identification numbers, a transmission/reception interface and a function to transmit/receive the luminance analysis result and/or stained moving image data specified by the identification numbers which are assigned via the transmission/reception interface may also be provided. Also, the transmission/reception interface and the means of receiving staining parameters generated by an external device via the transmission/reception interface and recording the parameters in the staining parameter recording section may also be provided.

Also, the ultrasonic diagnostic apparatus 100 comprises the image analyzing unit 200 in the above-described respective embodiments, but the image analyzing unit 200 may be an information processing device which is separate from the ultrasonic diagnostic apparatus, comprised in an information processing device capable of transmitting/receiving data to/from the ultrasonic diagnostic apparatus 100.

Such configuration enables, for example, performing luminance analyzing process in hospitals after contrast study on a PC with high processing capacity. Accordingly, temporal and spatial flexibility in luminance analyzing process can be improved.

Also, not only the entire function of the image analyzing unit 200 but also the entire or a part of the data recording unit 210 may be configured to be provided in an external storage unit. An external storage unit is a device such as an external hard disk, USB memory or CD-ROM.

For example, by comprising the staining parameter recording section 214 in an external storage device, a staining parameter can be easily changed to the one which is used in other displays. By doing so, it is possible to provide stained moving images having consistency with other analyses.

Also, comprising the luminance analysis result recording section 212 and the staining result recording section 213 in an external storage device can improve portability of the data therein.

DESCRIPTION OF REFERENCE NUMERALS

100 ultrasonic diagnostic apparatus
101 object
102 ultrasonic probe
103 ultrasonic transmission/reception unit
104 ultrasonic image constructing unit
105 video memory
106 display unit
107 operation unit
108 moving image recording unit
109 control unit
200 image analyzing unit
210 data storage unit
210*a* data storage unit
210*b* data storage unit
211 condition recording unit
212 luminance analysis result recording section
213 staining result recording section
214 staining parameter recording section
220 data processing unit
221 moving image obtaining section
222 analysis frame setting section
223 luminance analyzing section
224 staining section
225 moving image regenerating section
226 analysis frame determining section
227 record confirming section
300 analysis range specifying screen
310 moving image data display area
320 analysis range specifying area
321 starting frame display area
322 starting frame slider
323 ending frame slider
324 ending frame display area
400 color chart
410 time division
420 color

The invention claimed is:

1. An ultrasonic diagnostic apparatus comprising:
an ultrasonic probe configured to transmit/receive ultrasonic waves to/from an imaging target;
an ultrasonic transmitter/receptor configured to transmit ultrasonic waves, via the ultrasonic probe, and perform signal processing on reception signals from the ultrasonic probe;
an ultrasonic image constructor configured to chronologically construct ultrasonic images of a chronologically measured imaging target, based on the reception signals that are processed in the ultrasonic transmitter/receptor;
a display configured to chronologically display the chronologically constructed ultrasonic images;
a controller configured to control the ultrasonic transmitter/receptor, the ultrasonic image constructor and the display;
an operator configured to specify a time division of a staining commencement time when a contrast agent enters, for each pixel of the chronologically constructed ultrasonic images;
an image analyzer in the controller configured to:
determine a color assignment according to the time division of the staining commencement time, and
generate a contrast progress image by applying a color to the pixel of the ultrasonic images with the determined color assignment, wherein the image analyzer comprises:
a luminance analyzing section configured to:
specify a staining commencement time at which an inflow of the contrast agent reaches a predetermined luminance distribution by analyzing a luminance value of the chronologically constructed ultrasonic images,
extract a maximum value $l_{max}$ of a luminance in each pixel in an analysis range,
obtain a value $l_\alpha$ by multiplying the $l_{max}$ by a predetermined set threshold $\alpha$,
set a threshold value luminance attainment time $t_\alpha$, wherein the threshold value luminance attainment time $t_\alpha$ is a time that the luminance reaches the value $l_\alpha$, and
record the threshold luminance attainment time $t_\alpha$ obtained in each pixel as a luminance analysis result, and
a staining section configured to apply a predetermined color to the ultrasonic images that vary with time which are obtained after the specified staining commencement time; and
an analysis frame setter configured to set the analysis range in which the luminance analysis is performed by the luminance analyzing section.

2. The ultrasonic diagnostic apparatus according to claim 1, wherein the controller is further configured to superimpose contrast progress image on the ultrasonic image to be displayed on the display.

3. The ultrasonic diagnostic apparatus according to claim 2,
wherein the luminance analyzing section is further configured to chronologically measure the luminance of the contrast agent in a region of interest on the ultrasonic image; and wherein the controller is further configured to display the luminance variation curve and the superimposed image on the display.

4. The ultrasonic diagnostic apparatus according to claim 1, wherein the luminance analyzing section is further configured to determines an arrival time of the luminance capable of specifying a time difference of the inflow of the contrast agent, for each pixel of the ultrasonic images.

5. The ultrasonic diagnostic apparatus according to claim 4, wherein the luminance capable of specifying the time difference of the inflow of the contrast agent in the luminance analyzing section is acquired based on the maximum value $l_{max}$ of the luminance and a threshold value of the pixel.

6. The ultrasonic diagnostic apparatus according to claim 4, wherein the image analyzing section comprises:
   a condition recording section configured to receive a selection of the ultrasonic image for generating a stained ultrasonic image;
   a staining result recording section configured to record the stained ultrasonic image corresponding to an identification information for specifying the ultrasonic image; and
   a record confirming section configured to discriminate whether the stained ultrasonic image related to the selected ultrasonic image is recorded in the staining result recording section,
   wherein the controller, in response to the stained ultrasonic image which is related to the selected ultrasonic image is recorded in the staining result recording section, is further configured to display the recorded stained ultrasonic image on the display.

7. The ultrasonic diagnostic apparatus according to claim 1, wherein the analysis frame setter is further configured to:
   calculate a sum of signal intensities of all pixels for each of the ultrasonic images,
   calculate a difference of calculated sums between adjacent ultrasonic images, and
   set a first ultrasonic image, in response to the difference being greater than a predetermined value, as a starting image, and
   set a second ultrasonic image, in response to the difference being within a predetermined range and continues for more than a predetermined time, an ending image, wherein the second ultrasonic image is immediately after the predetermined time.

8. The ultrasonic diagnostic apparatus according to claim 1,
   wherein the image analyzer further comprises a staining parameter recording section configured to record a staining parameter table to store display colors for each division; and
   wherein the staining section is further configured to display each pixel with a display color stored in the staining parameter table corresponding to a division which is equivalent to a luminance attainment time of the contrast agent.

9. The ultrasonic diagnostic image according to claim 8, wherein:
   the staining parameter recording section is further configured to record a plurality of different staining parameter tables; and
   the staining section is further configured to display respective pixels using a staining parameter which is selected by an operator.

10. An image processing device which performs image analysis processing on chronologically constructed ultrasonic images obtained by an ultrasonic diagnostic apparatus, comprising:
   an operator configured to specify a time division of a staining commencement time at which contrast agent enters for each pixel of an ultrasonic image;
   an image analyzer configured to:
      determine a color assignment in accordance with the specified time division of the staining commencement time, and
      generate a contrast progress image, by applying a color to pixels of the ultrasonic image with the determined color assignment,
      wherein the image analyzer comprises:
         a luminance analyzing section configured to:
            specify a staining commencement time at which an inflow of the contrast agent reaches a predetermined luminance distribution by analyzing a luminance value of the chronologically constructed ultrasonic images,
            extract a maximum value $l_{max}$ of a luminance in each pixel in an analysis range,
            obtain a value $l_\alpha$ by multiplying the $l_{max}$ by a predetermined set threshold $\alpha$,
            set a threshold value luminance attainment time $t_\alpha$, wherein the threshold value luminance attainment time $t_\alpha$ is a time that the luminance reaches the value $l_\alpha$, and
            record the threshold luminance attainment time $t_\alpha$ obtained in each pixel as a luminance analysis result, and
         a staining section configured to apply a predetermined color to the ultrasonic images that vary with time which are obtained after the specified staining commencement time; and
   an analysis frame setter configured to set the analysis range in which the luminance analysis is performed by the luminance analyzing section.

11. A staining image generation method including:
   transmitting/receiving ultrasonic waves by a probe to/from an imaging target into which contrast agent is injected;
   constructing an ultrasonic image which chronologically varies on a basis of a signal received by the probe;
   specifying a time division of a staining commencement time at which the contrast agent enters for each pixel of the ultrasonic image;
   determining a color assignment in accordance with the specified time division of the staining commencement time, and
   generating a contrast progress image by applying a color to the pixels of the ultrasonic image with the determined color assignment;
   specifying a staining commencement time at which an inflow of the contrast agent reaches a predetermined luminance distribution by analyzing a luminance value of the chronologically constructed ultrasonic images;
   extracting a maximum value $l_{max}$ of a luminance in each pixel in an analysis range;
   obtaining a value $l_\alpha$ by multiplying the $l_{max}$ by a predetermined set threshold $\alpha$,
   setting a threshold value luminance attainment time $t_\alpha$, wherein the threshold value luminance attainment time $t_\alpha$ is a time that the luminance reaches the value $l_\alpha$, and
   recording the threshold luminance attainment time $t_\alpha$ obtained in each pixel as a luminance analysis result;

applying a predetermined color to the ultrasonic images that vary with time which are obtained after the specified staining commencement time; and setting an analysis range in which a luminance analysis is performed by a luminance analyzing section.

* * * * *